(12) United States Patent
Rosenberg et al.

(10) Patent No.: US 9,402,995 B1
(45) Date of Patent: Aug. 2, 2016

(54) SYSTEMS AND METHODS FOR COMBINED NEUROSTIMULATION AND DEFIBRILLATION THERAPY

(71) Applicant: PACESETTER, INC., Sylmar, CA (US)

(72) Inventors: Stuart Rosenberg, Castaic, CA (US); Wenbo Hou, Santa Clarita, CA (US); Timothy A. Fayram, Gilroy, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/603,064

(22) Filed: Jan. 22, 2015

(51) Int. Cl.
| | |
|---|---|
| A61N 1/00 | (2006.01) |
| A61N 1/08 | (2006.01) |
| A61N 1/39 | (2006.01) |
| A61N 1/36 | (2006.01) |
| A61N 1/05 | (2006.01) |

(52) U.S. Cl.
CPC ............. *A61N 1/08* (2013.01); *A61N 1/0551* (2013.01); *A61N 1/36182* (2013.01); *A61N 1/3918* (2013.01); *A61N 1/3956* (2013.01)

(58) Field of Classification Search
CPC ..... A61N 1/08; A61N 1/0551; A61N 1/3918; A61N 1/3956; A61N 1/046; A61N 1/0563; A61N 1/362; A61N 1/39
See application file for complete search history.

(56) References Cited

U.S. PATENT DOCUMENTS

| | | | | |
|---|---|---|---|---|
| 2006/0122649 A1* | 6/2006 | Ghanem | ............... | A61N 1/05 607/9 |
| 2008/0033260 A1* | 2/2008 | Sheppard | ........... | A61N 1/36557 600/301 |
| 2009/0191087 A1* | 7/2009 | Klein | ................ | C22C 5/04 420/463 |
| 2010/0114195 A1* | 5/2010 | Burnes | ............... | A61N 1/0504 607/4 |
| 2012/0303084 A1* | 11/2012 | Kleckner | ........... | A61N 1/36114 607/25 |

\* cited by examiner

*Primary Examiner* — Robert N Wieland

(57) ABSTRACT

The present disclosure provides systems and methods for providing both neurostimulation and defibrillation therapy. The system includes an implantable pulse generator (IPG), at least one neurostimulation electrode electrically coupled to the IPG and configured to apply neurostimulation pulses to a subject, and at least one defibrillation electrode electrically coupled to the IPG and configured to apply defibrillation pulses to the subject.

7 Claims, 13 Drawing Sheets

SYSTEMS AND METHODS FOR COMBINED NEUROSTIMULATION AND DEFIBRILLATION THERAPY

FIELD OF THE DISCLOSURE

This disclosure relates to systems and methods for neurostimulation and defibrillation, and more particularly to providing both neurostimulation and defibrillation therapy using a single system.

BACKGROUND ART

Many tachyarrhythmias are mediated at least in part by the autonomic nervous system (ANS) of a subject, or patient. Accordingly, targeting the ANS for treating cardiac arrhythmias is of increasing interest. For example, application of spinal cord stimulation (SCS) to cardiac diseases is of particular interest. In fact, it has been demonstrated that thoracic SCS may alter electrophysiologic properties of both the left and right atriums, and may slow the onset of atrial fibrillation (AF). Further, SCS has proven efficacy for treating angina pectoritis.

Subjects for which SCS is utilized to treat cardiac symptoms typically have an implantable cardioverter-defibrillator (ICD) or cardiac resynchronization therapy pacemaker with defibrillation therapy (CRT-D) already implanted at the time of SCS system implantation. Accordingly, current therapy systems require both an ICD-type device and a separate neuromodulation system to treat heart failure (HF) and/or arrhythmia using SCS methods. However, this may be relatively expensive, as both ICD systems and SCS systems are relatively expensive. Further, while ICDs are typically utilized for life-saving therapy, SCS systems are generally used for palliative therapy/symptom relief.

Even if SCS is a viable treatment option for HF, it is possible that the resultant reduction of tachyarrhythmias will not be complete, and that patients using SCS for anti-tachycardia indications would still require some form of redundant, or "backup" protection in the event arrhythmia occurs. Further, even if neurostimulation is shown to reduce HF symptom severity significantly, many recipients of the SCS therapy would still be candidates for an ICD.

BRIEF SUMMARY OF THE DISCLOSURE

In one embodiment, a combined neurostimulation and defibrillation system is provided. The system includes an implantable pulse generator (IPG), at least one neurostimulation electrode electrically coupled to the IPG and configured to apply neurostimulation pulses to a subject, and at least one defibrillation electrode electrically coupled to the IPG and configured to apply defibrillation pulses to the subject.

In another embodiment, a method for implanting a combined neurostimulation and defibrillation system in a subject is provided. The method includes positioning the subject on an operating table, implanting at least one lead within the subject, the at least one lead including at least one neurostimulation electrode configured to apply neurostimulation pulses to the subject and at least one defibrillation electrode configured to apply defibrillation pulses to the subject, testing operation of the at least one lead, implanting an implantable pulse generator (IPG) in the subject, and connecting the at least one lead to the IPG.

In another embodiment, the present disclosure is directed to a lead for use in a combined neurostimulation and defibrillation system. The lead includes at least one neurostimulation electrode configured to apply neurostimulation pulses to a subject, and at least one defibrillation electrode configured to apply defibrillation pulses to the subject.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The disclosure provides systems and methods for a combining neurostimulation and defibrillation capabilities into a single device. For example, in some embodiments, the device combines the functions of a subcutaneous ICD (S-ICD) and a neurostimulator. The device is less invasive than a transvenous ICD and avoids the cost and increased potential complications of having two separate systems.

In one example, a combined neurostimulation and defibrillation system includes a set of defibrillation electrodes positioned on the chest of the subject (e.g., near the sternum and on the left side of the rib cage) that allow for sensing of heart rhythm and delivery of a defibrillation shock when required. The system also includes a set of neurostimulation electrodes on the chest (e.g., subcutaneously), back, or spine that allow for programmable neurostimulation to treat the heart, such as anti-arrhythmia stimulation, anti-angina stimulation, and/or autonomic-modulating stimulation. For example, activation of cutaneous nerve fibers in the thoracic region, consistent with dermatomes affected by angina, will modulate the same neural pathways as dorsal column stimulation covering those dermatomes.

The system's neurostimulation functionality provides neurostimulation that facilitates reducing the likelihood of arrhythmias by means of short- and long-term electrophysiologic substrate modulation via modulation of the autonomic nervous system. The neurostimulation functionality may be always-on, triggered, or on-demand. Further, the system performs heart rhythm monitoring, and upon detection of arrhythmia, the neurostimulation is maintained, altered, or stopped, and a shock is delivered as needed to cardiovert or defibrillate.

Figure 1:
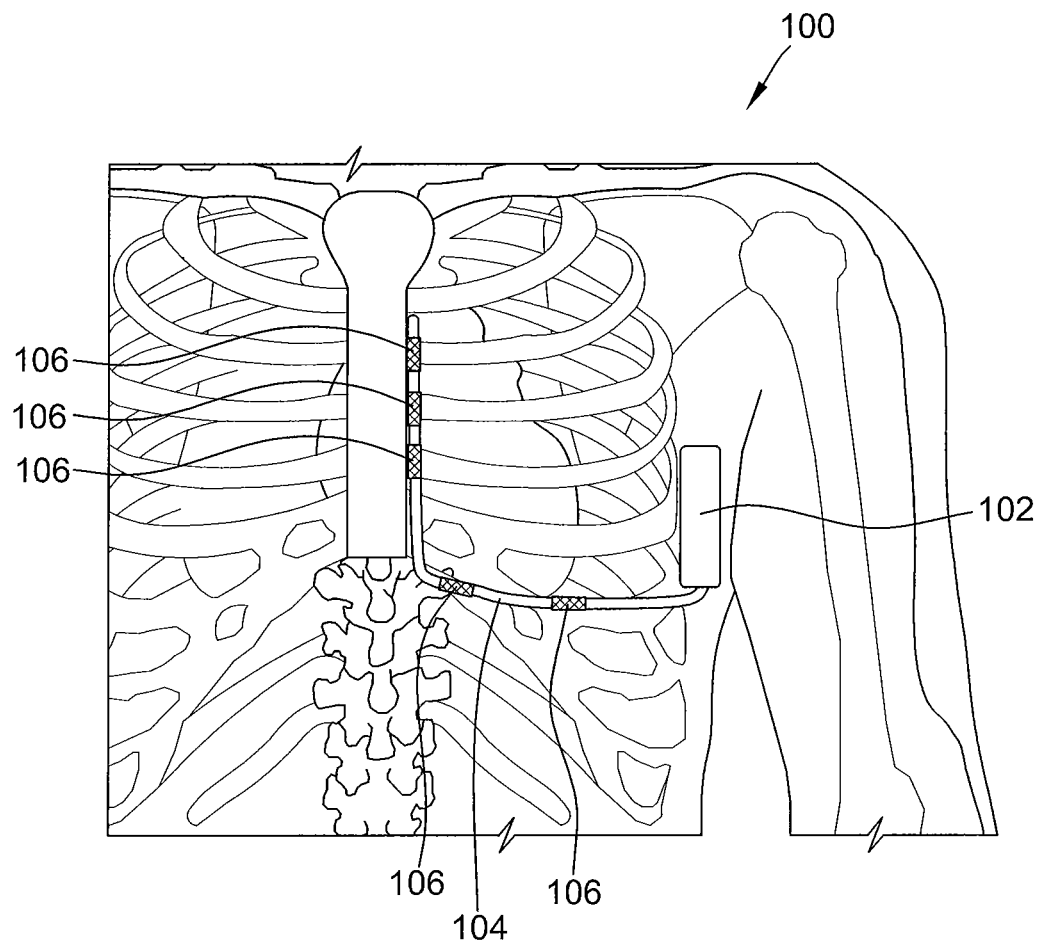
FIG. 1 is a schematic diagram of a combined neurostimulation and defibrillation system according to one embodiment.

Referring now to the drawings wherein like reference numerals are used to identify identical components in the various views, FIG. 1 illustrates one embodiment of a combined neurostimulation and defibrillation system 100. System 100 includes an implantable pulse generator (IPG) 102 includes associated electronics and/or logic for cardiac rhythm sensing (including detection/discrimination for tachyarrhythmias), as well as controls for delivery of neurostimulation and defibrillation therapy.

Figure 2:
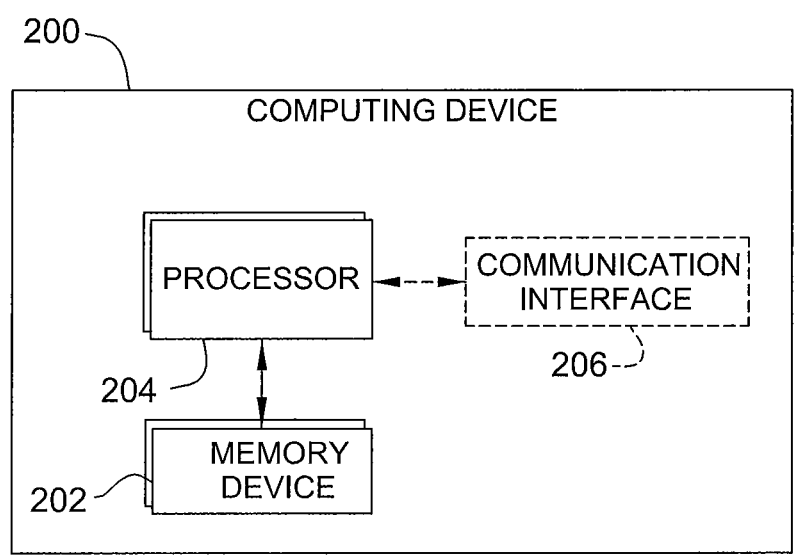
FIG. 2 is a block diagram of a computing that may be used with the system shown in FIG. 1.

For example, FIG. 2 is a block diagram of a computing device 200 that may be implemented within IPG 102. Computing device 200 facilitates controlling system 100 for delivery of neurostimulation and defibrillation therapy, as described herein. Those of skill in the art will appreciate that computing device 200 may be implemented in other embodiments described herein.

Computing device 200 includes at least one memory device 202 and a processor 204 that is coupled to memory device 202 for executing instructions. Executable instructions are stored in memory device 202. Computing device 200 performs one or more operations described herein by programming processor 204. For example, processor 204 may be programmed by encoding an operation as one or more executable instructions and by providing the executable instructions in memory device 202.

Processor 204 may include one or more processing units (e.g., in a multi-core configuration). Further, processor 204 may be implemented using one or more heterogeneous processor systems in which a main processor is present with secondary processors on a single chip. In another illustrative example, processor 204 may be a symmetric multi-processor system containing multiple processors of the same type. Further, processor 204 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, memory device 202 is one or more devices that enable information such as executable instructions and/or other data to be stored and retrieved. Memory device 202 may include one or more computer readable media, such as, without limitation, dynamic random access memory (DRAM), static random access memory (SRAM), a solid state disk, and/or a hard disk. Memory device 202 may be configured to store, without limitation, application source code, application object code, source code portions of interest, object code portions of interest, configuration data, execution events and/or any other type of data.

Computing device 200, in the illustrated embodiment, includes a communication interface 206 coupled to processor 204. Communication interface 206 communicates with one or more remote devices, such as a clinician or patient programmer. To communicate with remote devices, communication interface 206 may include, for example, a wired network adapter, a wireless network adapter, a radio-frequency (RF) adapter, a Bluetooth® adapter (Bluetooth is a registered trademark of Bluetooth SIG, Inc., a Delaware corporation), and/or a mobile telecommunications adapter.

Referring back to FIG. 1, in this embodiment, system 100 includes a lead 104 having a plurality of electrodes 106. Each electrode 106 is capable of functioning as a neurostimulation electrode (i.e., by applying neurostimulation electrical pulses) and at least some of the electrodes 106 are capable of functioning as a defibrillation electrode (i.e., by applying defibrillation electrical pulses/shocks). In other embodiments, such as those described below, system 100 may include multiple leads having dedicated neurostimulation leads electrodes and dedicated defibrillation leads electrodes. The neurostimulation electrodes, in conjunction with IPG 102, essentially form a shocking vector and function as an S-ICD, and the defibrillation electrodes, in conjunction with IPG 102, essentially function as a neurostimulation system, as described herein.

Figure 3:
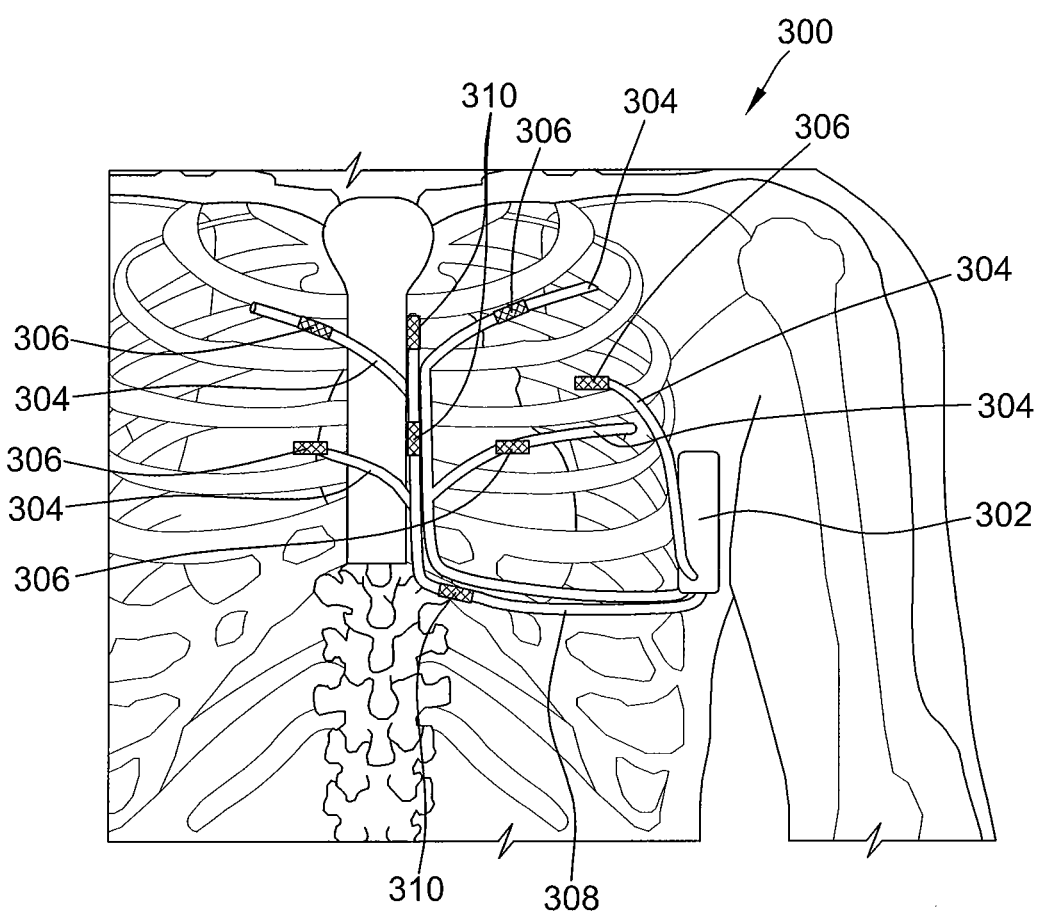
FIG. 3 is a schematic diagram of an alternative combined neurostimulation and defibrillation system.

FIG. 3 is a schematic diagram of an alternative combined neurostimulation and defibrillation system 300. Similar to system 100 (shown in FIG. 1), system 300 includes an IPG 302. However, in contrast to system 100, system 300 includes first leads 304 including dedicated neurostimulation electrodes 306, and second leads 308 including dedicated defibrillation electrodes 310.

Figure 4:
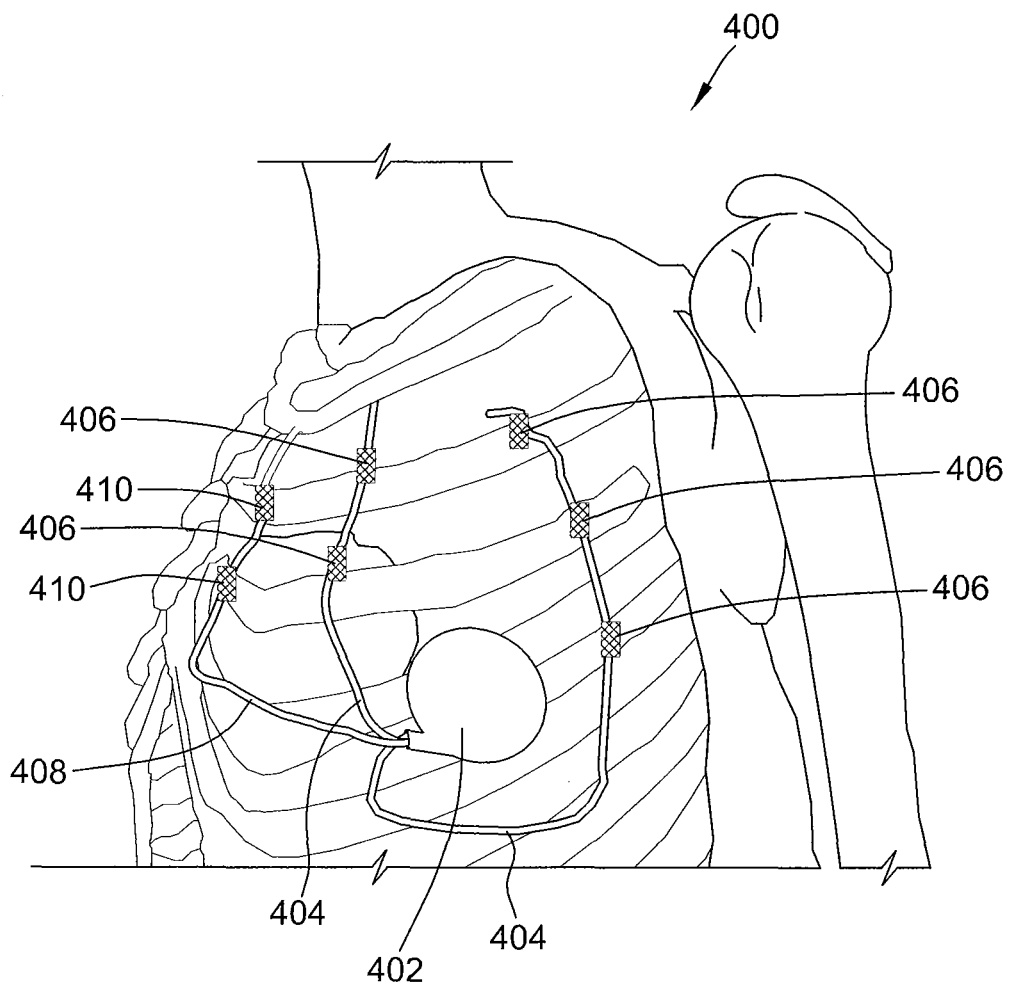
FIG. 4 is a schematic diagram of an alternative combined neurostimulation and defibrillation system.

FIG. 4 is a schematic diagram of another alternative combined neurostimulation and defibrillation system 400. System 400 includes an IPG 402, first leads 404 including dedicated neurostimulation electrodes 406 positioned to stimulate cutaneous nerves of the thorax, and second leads 408 including dedicated defibrillation electrodes 410.

Figure 5:
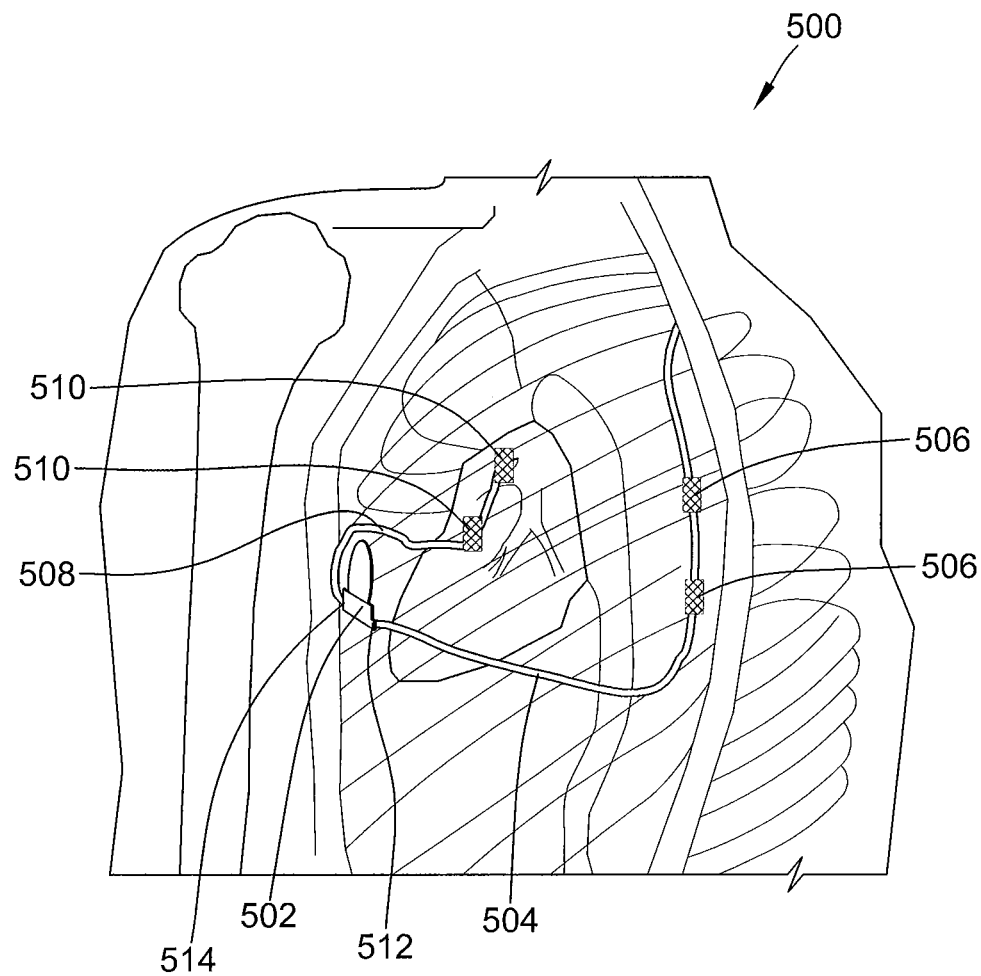
FIG. 5 is a schematic diagram of an alternative combined neurostimulation and defibrillation system.

FIG. 5 is a schematic diagram of yet another alternative combined neurostimulation and defibrillation system 500. System 500 includes an IPG 502, first leads 504 including dedicated neurostimulation electrodes 506, and second leads 508 including dedicated defibrillation electrodes 510. In system 500, to facilitate minimizing a lead tunneling pathway, first leads 504 are connected to a posterior port 512 of IPG 502, and second leads 508 are connected to an anterior port 514 of IPG 502.

In systems 100, 300, and 400, electrodes for neurostimulation are positioned to stimulate cutaneous thoracic nerves whose signals are transmitted to the thoracic spinal cord. In system 500, at least some electrodes for neurostimulation are positioned to stimulate thoracic spinal nerve roots where they exit the spinal column, transmitting electrical signals to the spinal cord more directly than in systems 100 and 300. Stimulation of thoracic nerve networks modulates autonomic balance, for example, blunting excess activity of the stellate ganglia and cardiac ganglia. Further, stimulation of thoracic nerve networks modulates central nervous responses by propriospinal and supraspinal pathways, further modulating sympathetic outflow to the thoracic ganglia and parasympathetic output to the heart through the vagus nerve.

Figure 6A:
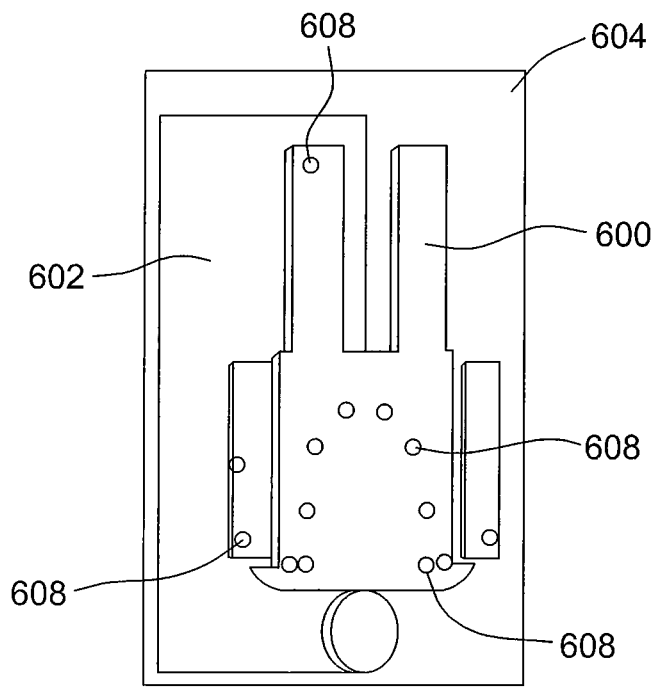
FIG. 6A is a top schematic view of a patient on an operating table according to one embodiment.
Figure 6B:
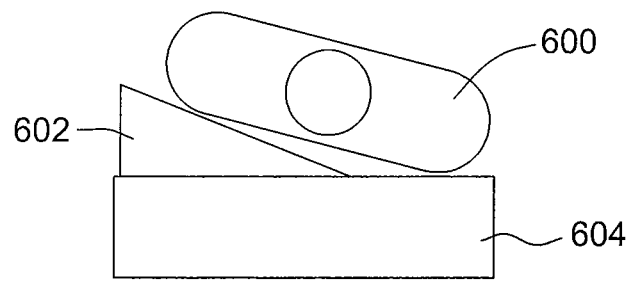
FIG. 6B is a top schematic view of a patient on an operating table.

For systems 100 and 300, all leads may be implanted while a patient is supine. For system 400, leads may be implanted while a patient is supine. Alternatively, performing the implantation with a wedge positioned under the left shoulder and flank of the patient such that the patient is at an approximately thirty degree rotated recumbency may be advantageous, as it provides an ergonomic advantage for the operator performing the implantation. For example, FIG. 6A is a top schematic view of a patient 600 supported by a wedge 602 on an operating table 604, and FIG. 6B is a side schematic view of patient 600, wedge 602, and operating table 604. As shown in FIG. 6A, a number of electrodes 608 (e.g., electrocardiographic (EKG) and electromyographic (EMG)) electrodes are attached to patient 600 for monitoring patient 600 during the implantation procedure.

For system 500, as well as for similar configurations (not shown) where a neurostimulation lead is placed percutaneously in the epidural space to stimulate the dorsal column (i.e., for conventional SCS) and then tunneled to an IPG on the left chest, implantation may be accomplished by rolling the patient and re-establishing a sterile field, or by two separate procedures (i.e., one procedure for implantation of IPG 502 and second leads 508, and a second procedure for implantation of first leads 504.

In other embodiments, traditional neuromodulation leads (e.g., cylindrical leads or paddle leads) may be implanted in the epidural space of the spinal cord. For example, a neuromodulation lead may be positioned around the T1 vertebrae and then tunneled into a pocket for the IPG. Using such a configuration, therapy may be delivered by stimulating the dorsal column.

In another alternative embodiment, a mat electrode array (not shown) may be implanted over the sternum to yield peripheral nerve stimulation similar to that of system 300 (shown in FIG. 3). The mat electrode replaces four of the first leads 304 and facilitates simplifying the subcutaneous implantation procedure. Stimulation patterns for electrodes in the mat electrode array are programmable and may be reconfigured (e.g., using a clinician programmer or a patient programmer in communication with the IPG).

In yet another alternative embodiment, a mat electrode array is implanted subcutaneously on a side of the patient's rib cage in close proximity to the IPG. This yields a different peripheral nerve stimulation than system 300 and rather more like that of system 400. The mat electrode array may further be tucked around the back of the patient in a location relatively close to the thoracic spinal cord region, similar to system 500.

In yet another alternative embodiment, the neurostimulation electrodes may be leadless electrodes. That is, each neurostimulation electrode may include a receiver that is powered wirelessly by the IPG to deliver neurostimulation therapy. Further, in some embodiments, the neurostimulation electrodes are in wireless communication with an S-ICD.

Example embodiments for implanting a combined neurostimulation and defibrillation system (such as systems 100, 300, 400, and 500) will now be described. For the system to function properly, the system must be capable of providing appropriately targeted neurostimulation, sensing cardiac rhythm, and cardioverting/defibrillating detected cardiac arrhythmias.

Figure 7A:
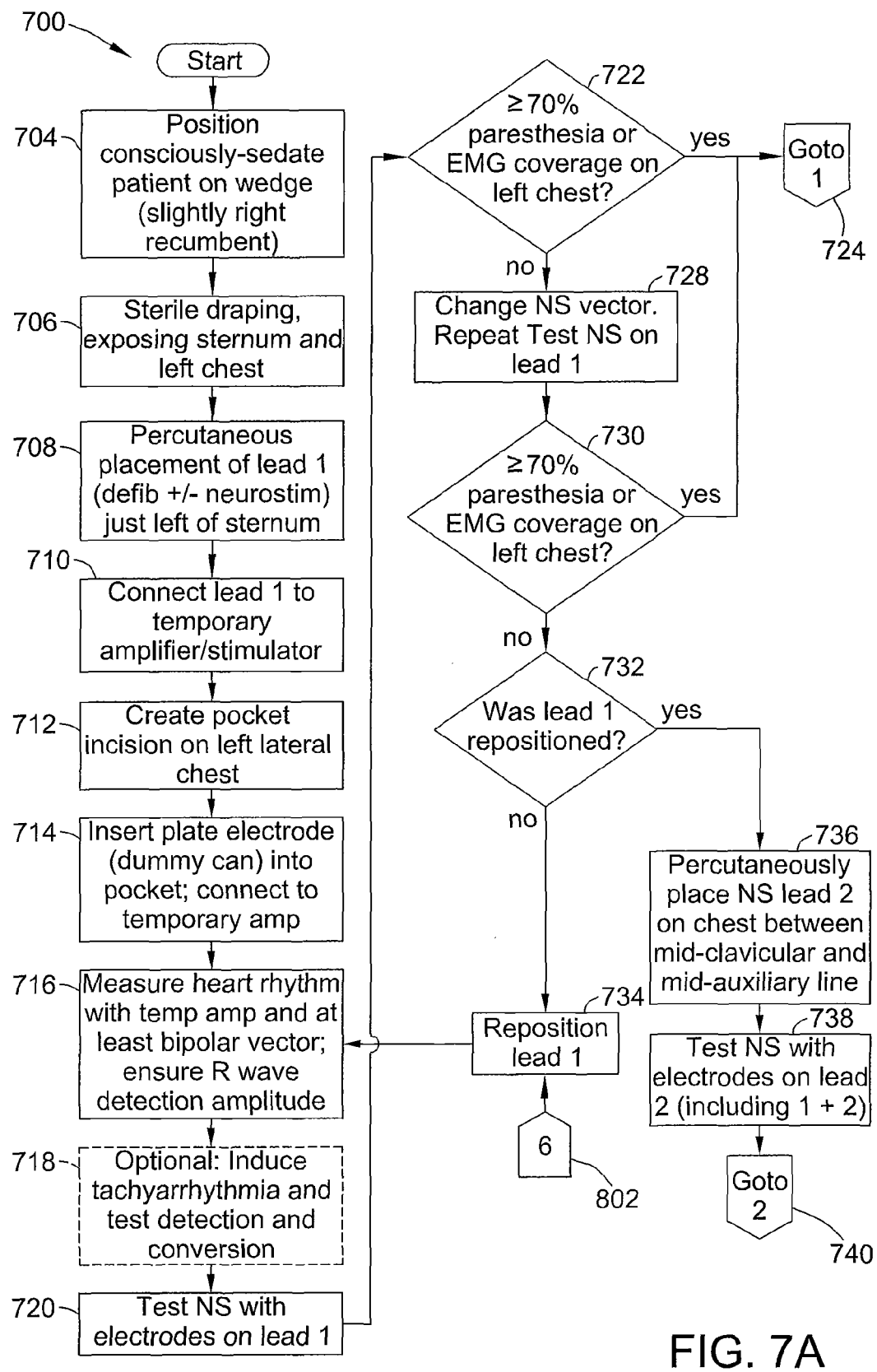
FIGS. 7A-7C are flow diagrams illustrating a method of implanting a combined neurostimulation and defibrillation system according to one embodiment.
Figure 7B:
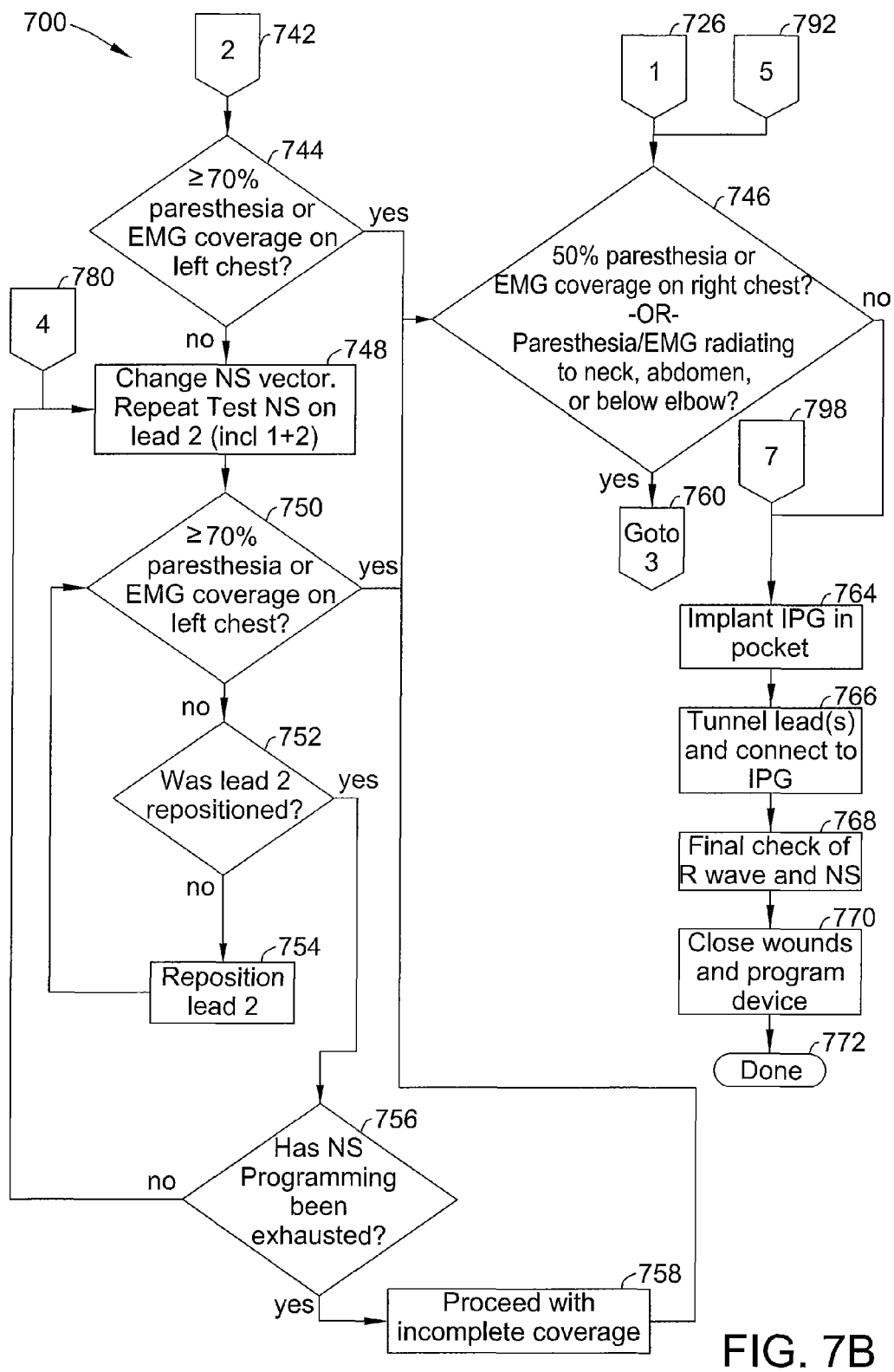
Figure 7C:
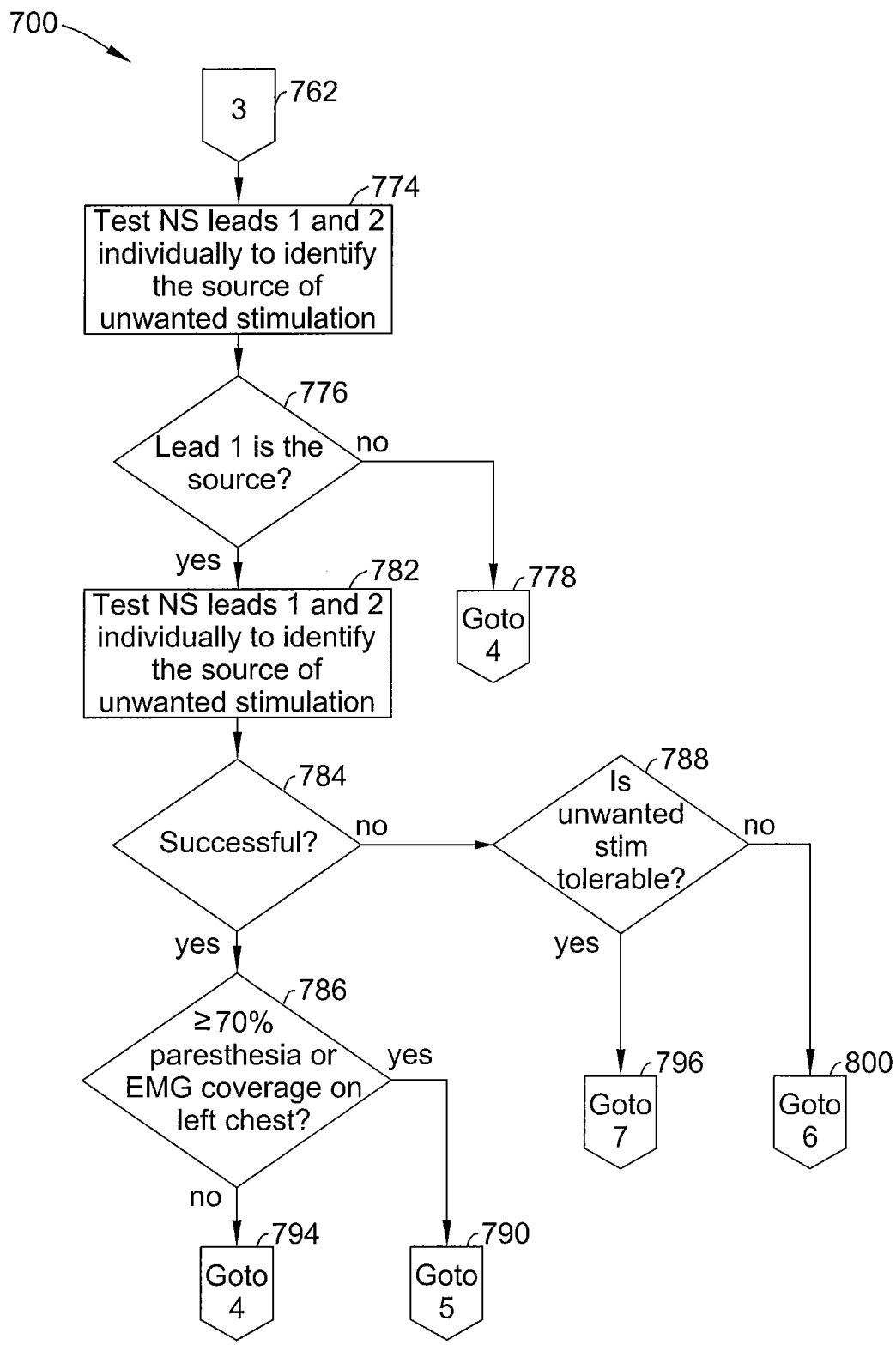

FIGS. 7A-7C are collectively a flow diagram of a method 700 for implanting a combined neurostimulation and defibrillation system. The method starts at block 702. At block 704, a consciously-sedate patient is positioned on a wedge, such as wedge 602 (shown in FIGS. 6A and 6B) such that the patient is slightly right recumbent. At block 706, sterile draping is applied to establish a sterile field, and the sternum and left chest of the patient are exposed.

At block 708, a first defibrillation and/or neurostimulation lead ("lead 1"), such as the leads described in reference to FIGS. 1, 3, 4, and 5, is percutaneously positioned to the left of the sternum. In this embodiment, the first lead includes at least one electrode configured to record precordial cardiac electric signals. At block 710, the first lead is connected to a temporary amplifier/stimulator. At block 712, a pocket incision is made on the left lateral chest of the patient, approximately over the apex of the patient's heart.

At block 714, a plate electrode is electrically coupled to the temporary amplifier/stimulator and inserted into the pocket made in block 712. Alternatively, an IPG is inserted into the pocket and the case electrode of the IPG is electrically coupled to the temporary amplifier/stimulator. At block 716, the heart rhythm of the patient is measured with the temporary amplifier/stimulator, a bipolar pace vector is measured, and R wave amplitude detection is verified.

At block 718, optionally, a cardioversion or defibrillation test may be performed (e.g., by inducing tachyarrhythmia and testing detection and conversion). Based on the data acquired at blocks 716 and 718, the location of the first lead and/or the pocket may be adjusted.

At block 720, neurostimulation capabilities for the first lead are tested. For example, stimulation at 50 Hertz (Hz) may be delivered (e.g., with a voltage amplitude of a few volts and/or a current amplitude of a few milliamps) through one or more electrodes on the first lead while asking the patient for verbal feedback on paresthesia. Optionally, an electromyogram of the intercostal muscles and heart rate variability may be concurrently measured to assess appropriate dermatome coverage and possible effects on autonomic modulation, respectively. Further optionally, an electromyogram of the arms, neck, and/or abdomen of the patient may be concurrently measured to avoid inappropriate dermatome coverage for the neurostimulation.

At block 722, it is determined whether the neurostimulation test at block 720 yields at least 70% paresthesia or EMG coverage on the left chest, which is desirable. If so, flow proceeds to block 724, which links to block 726 (shown in FIG. 7B). If not, flow proceeds to block 728, where a neurostimulation vector is changed, and the neurostimulation test is repeated for the first lead. At block 730, it is determined whether the neurostimulation test at block 728 yields at least 70% paresthesia or EMG coverage on the left chest. If so, flow proceeds to block 724. If not, flow proceeds to block 732. Optionally, the neurostimulation vector changing and neurostimulation test of block 728 and the determination of block 730 may be repeated (i.e., looped) for additional possible neurostimulation vectors before proceeding to block 724 or 732 accordingly.

At block 732, it is determined whether the first lead has been repositioned. If not, flow proceeds to block 734, where the first lead is repositioned, and then flow returns to block 716; it should be appreciated that appropriate R wave sensing/detection is important for patient safety, and once the first lead is repositioned at block 734, the performance of detection must be verified. If so, flow proceeds to block 736, where a second lead is placed percutaneously on the chest of the patient between the mid-clavicular line and the mid-axillary line and directed cranially. Alternatively, the second lead may be positioned directly along the mid-axillary line, with a distal portion of the second lead directed slightly medially so as to facilitate covering as many cutaneous nerve trees as possible. At block 738, neurostimulation capabilities for the second lead are tested along with the first lead (similar to block 720), and flow proceeds to block 740, which links to block 742 (shown in FIG. 7B).

From block 742, flow proceeds to block 744, where it is determined whether the neurostimulation test for the first and second leads at block 738 yields at least 70% paresthesia or EMG coverage on the left chest. If so, flow proceeds to block 746, which is described below. If not, flow proceeds to block 748, where a neurostimulation vector is changed, and the neurostimulation test is repeated for the first and second leads. At block 750, it is determined whether the neurostimulation test at block 748 yields at least 70% paresthesia or EMG coverage on the left chest. If so, flow proceeds to block 746. If not, flow proceeds to block 752.

At block 752, it is determined whether the second lead has been repositioned. If not, flow proceeds to block 754, where the second lead is repositioned, and then flow returns to block 750; it should be appreciated that since the second lead is only used for neurostimulation and not for R wave detection, ability of the system to sense cardiac signals need not be re-evaluated upon moving the second lead at bock 754. If so, flow proceeds to block 756, where it is determined whether possible neurostimulation programming options have been exhausted. If not, flow returns to block 748. If so, flow proceeds to block 758, and method 700 proceeds to block 746 with incomplete coverage.

At block 746, it is determined whether i) there is greater than 50% paresthesia or EMG coverage on the right chest of the patient, or ii) paresthesia/EMG is radiating to the neck or abdomen, or below the elbow of the patient, either of which is undesirable. This is to ensure that the implanted system is not overstimulating the patient or making the patient uncomfortable. If either of these conditions is satisfied, flow proceeds to block 760, which is linked to block 762 (shown in FIG. 7C). If neither of these conditions is satisfied, flow proceeds to blocks 764, where the IPG is implanted in the pocket.

At block 766, the first and (if present) second leads are connected to the IPG, and at block 768, final checks for monitoring the R wave and neurostimulation are performed. At block 770, the wounds in the patient at lead and IPG insertion sites are closed and the IPG is programmed, and method 700 ends at block 772.

Referring to FIG. 7C, from block 762, flow proceeds to block 774, where the first and second leads are tested individually to identify the source of the undesirable stimulation. At block 776, it is determined whether the first lead is the source. If the first lead is not the source, flow proceeds to block 778, which is linked to block 780 (shown in FIG. 7B). If the first lead is the source, the first lead is reprogrammed at block 782 to avoid the undesirable stimulation.

At block 784, it is determined whether the reprogramming at block 782 was successful. If the reprogramming was successful, flow proceeds to block 786. If the reprogramming was not successful, flow proceeds to block 788.

At block 786, it is determined whether there is at least 70% paresthesia or EMG coverage on the left chest. If so, flow proceeds to block 790, which is linked to block 792 (shown in FIG. 7B). If not, flow proceeds to block 794, which is linked to block 780 (shown in FIG. 7B).

At block 788, it is determined whether the undesirable stimulation is tolerable. If so, flow proceeds to block 796, which is linked to block 798 (shown in FIG. 7B). If not, flow proceeds to block 800, which is linked to block 802 (shown in FIG. 7A).

Notably, method 700 is one example of a method for implanting a combined neurostimulation and defibrillation system. Those of skill in the art will appreciate that variations and/or modifications may be made to method 700 without departing from the spirit and scope of the disclosure.

Figure 8A:
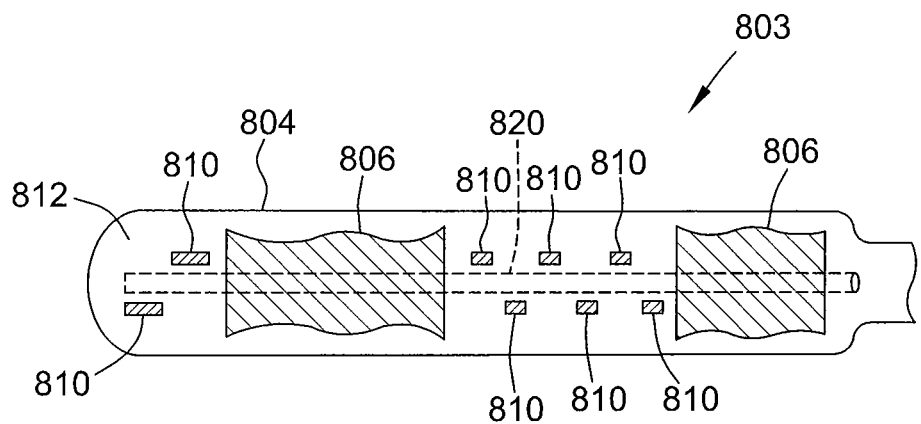
FIG. 8A is a bottom schematic view of a lead according to one embodiment.
Figure 8B:
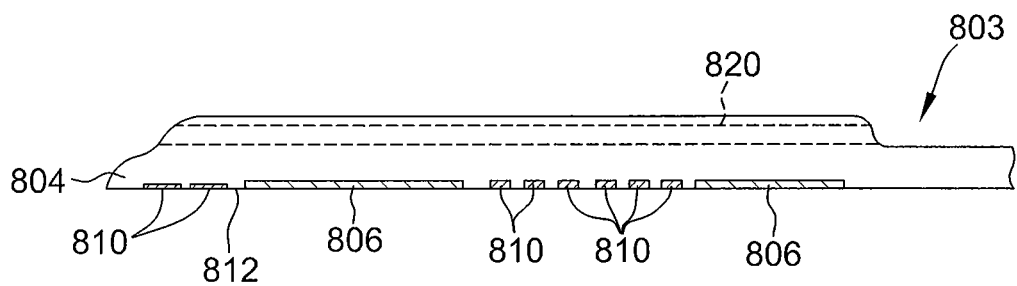
FIG. 8B is a side schematic view of the lead shown in FIG. 8A.
Figure 8C:
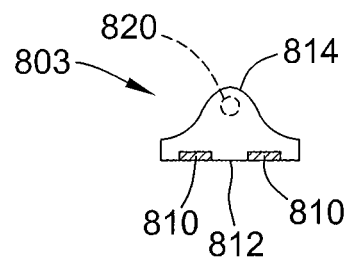
FIG. 8C is an end schematic view of the lead shown in FIG. 8A.

FIGS. 8A-8C are schematic views of one embodiment of a combined neurostimulation and defibrillation lead 803 that may be used with the combined neurostimulation and defibrillation systems described herein. Specifically, FIG. 8A is a schematic bottom view of lead 803, FIG. 8B is a schematic side view of lead 803, and FIG. 8C is a schematic end view of lead 803.

In this embodiment, lead 803 includes a distal portion 804 having two defibrillation electrodes 806. To facilitate uniform current density, each defibrillation electrode 806 is relatively large (e.g., having a length between approximately 15 and 50 millimeters (mm)), flat, and flexible. Further, in this embodiment, defibrillation electrodes 806 are spaced apart from one another a distance between approximately 28 and 70 mm. Alternatively, lead 803 may have any suitable number and/or configuration of defibrillation electrodes 806. In this embodiment, in addition to applying defibrillation therapy, defibrillation electrodes 806 are also used for cardiac rhythm sensing. Further, defibrillation electrodes 806 may be used as anodes for neurostimulation, provided that the IPG has appropriate blanking functionality. As used herein, 'blanking' refers to eliminating all applied electrical stimulation at an electrode before initiating sensing.

As shown in FIG. 8A, lead 803 includes neurostimulation electrodes 810 positioned distally beyond defibrillation electrodes 806, and in between defibrillation electrodes 806. In this embodiment, lead 803 includes eight neurostimulation electrodes 810, and each neurostimulation electrode 810 is rectangular and a relatively small, targeted electrode (e.g., having a length between approximately 1 and 6 mm). Further, neurostimulation electrodes 810 are arranged in sets of two or three electrodes to facilitate shaping of the applied electric field. Alternatively, neurostimulation electrodes 810 may have any suitable shape (e.g., circular), number, and/or configuration that enables lead 803 to function as described herein.

Distal portion 804 includes a flat surface 812 and an opposite rounded surface 814. Further, a lumen 820 is defined through distal portion 801. In this embodiment, lumen 820 extends parallel to a midline of distal portion 801. Alternatively, lumen 820 may have any location that enables lead 803 to function as described herein. Lumen 820 is configured to receive a stylet (not shown) during the implantation procedure to facilitate positioning lead 803. For example, this facilitates pushing lead 803 under the skin of the patient through an incision near the bottom of the patient's rib cage. In this embodiment, a proximal portion (not shown) of lead 803 is round, with conductors arranged in a spiral fashion. As will be appreciated by those of skill in the art, a proximal end of lead 803 includes one or more connectors (not shown) to plug into the IPG.

Figure 9:
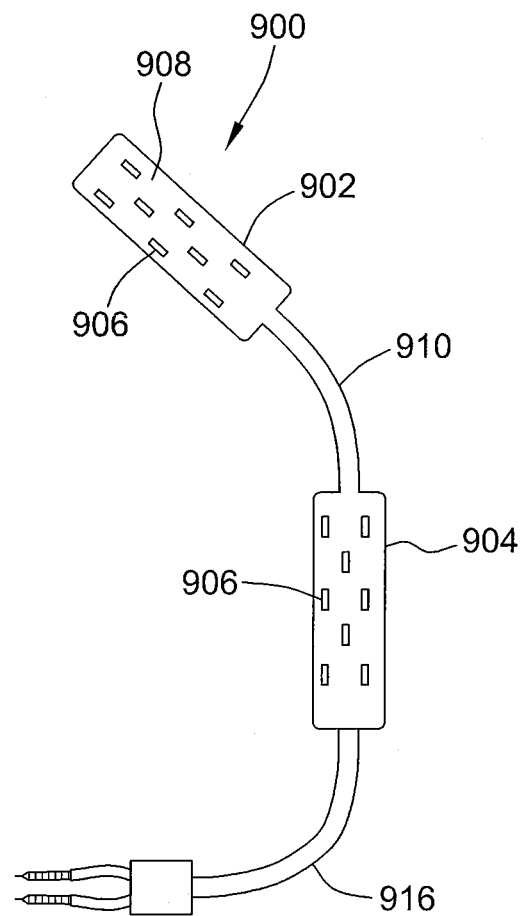
FIG. 9 is a schematic view of a lead according to one embodiment.

FIG. 9 is a schematic view of an alternative embodiment of a lead 900 that may be used with the combined neurostimulation and defibrillation systems described herein. Lead 900 includes a distal electrode section 902 and a proximal electrode section 904. Electrode sections 902 and 904 each include a plurality of electrodes 906. Although only neurostimulation electrodes are shown in FIG. 9, lead 900 may include any suitable arrangement of neurostimulation and/or defibrillation electrodes.

Similar to lead 803, each electrode section 902 and 904 includes a flat surface 908 containing electrodes 906 and an opposite rounded surface 909 (shown in FIGS. 10 and 11). Electrode sections 902 and 904 are connected by a first substantially cylindrical intermediate section 910. Further, connectors 914 for plugging into the IPG are included at a proximal end of lead 900 and coupled to proximal electrode section 904 through a second substantially cylindrical intermediate section 916.

Intermediate sections 910 and 916 are relatively flexible in all directions, and may be fabricated from polymers having a high elongation and a low modulus. Further, conductors running through intermediate sections 910 and 916 may be arranged in a loose spiral to promote flexibility.

In contrast, in this embodiment, electrode sections 902 and 904 are flexible in a single direction. Proximate rounded surfaces 909, each electrode section 902 and 904 includes one or more lumens that receive a stylus to facilitate positioning electrode sections 902 and 904.

Figure 10A:
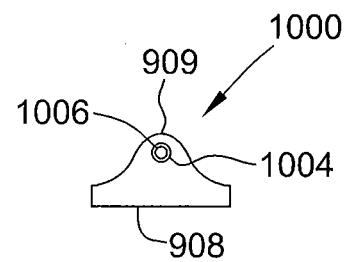
FIG. 10A is a schematic end view of a lumen configuration for the lead shown in FIG. 9 according to one embodiment.
Figure 10B:
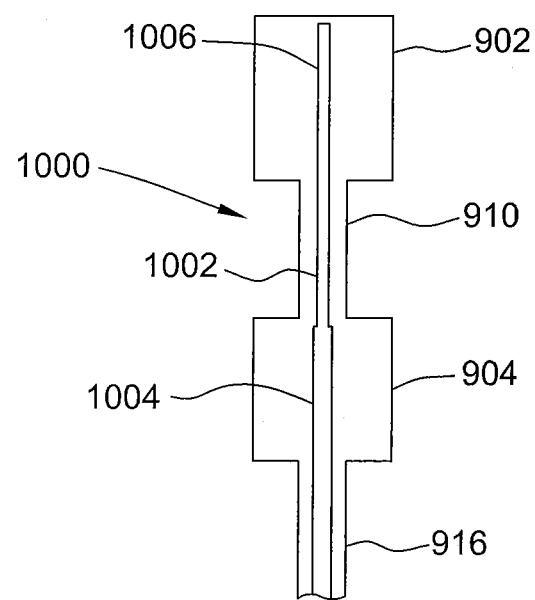
FIG. 10B is a schematic top view of the lumen configuration shown in FIG. 10A.
Figure 11A:
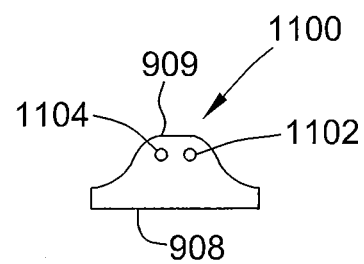
FIG. 11A is a schematic end view of an alternative lumen configuration.
Figure 11B:
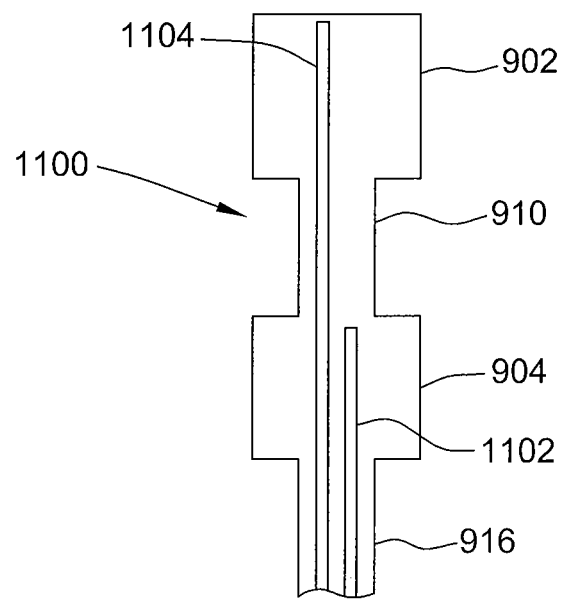
FIG. 11B is a schematic top view of the alternative lumen configuration shown in FIG. 11A.

FIGS. 10A and 10B are schematic end and top views, respectively, of a first lumen configuration 1000 that may be used with lead 900. FIGS. 11A and 11B are end and top views, respectively, of a second lumen configuration 1100 that may be used with lead 900.

First lumen configuration 1000 includes a single lumen 1002 extending through second intermediate section 916, proximal electrode section 904, first intermediate section 910, and distal electrode section 902. Lumen 1002 includes a large diameter section 1004 that terminates within proximal electrode section 904, and a small diameter section 1006 that terminates within distal electrode section 902. Lumen 1002 facilitates positioning electrode sections 902 and 904 independent of one another before tunneling connectors 914 to the IPG. Specifically, a first, large diameter stylet may be used in conjunction with large diameter section 1004 to position proximal electrode section 904, and a second, small diameter stylet may be used in conjunction with small diameter section 1006 to position distal electrode section 902.

Second lumen configuration 1100 includes a first lumen 1102 that terminates within proximal electrode section 904, and a second lumen 1104 that terminates within distal electrode section 902. First and second lumens 1102 and 1104 facilitate positioning electrode sections 902 and 904 independent of one another before tunneling connectors 914 to the IPG. Specifically, a first stylet may be used in conjunction with first lumen 1102 to position proximal electrode section 904, and a second stylet may be used in conjunction with second lumen 1104 to position distal electrode section 902.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A combined neurostimulation and defibrillation system comprising:
    an implantable pulse generator (IPG);
    a stimulation lead adapted for connection to the IPG, wherein the stimulation lead comprises a first flat surface and a second flat surface, a connector portion for connecting to the IPG, a first intermediate portion between the connector portion and the first flat surface, and a second intermediate portion between the first flat surface and the second flat surface;
    wherein each of the first flat surface and second flat surfaces comprise at least one neurostimulation electrode adapted to apply neurostimulation pulses from the IPG to a patient and at least one defibrillation electrode for applying defibrillation pulses from the IPG to the patient;
    wherein the first and second intermediate portions comprise first and second lumens to receive stylets for independent positioning of the first and second flat surfaces during implantation of the stimulation lead in the patient through a single incision.

2. The system of claim 1 wherein each of the first and second flat surfaces comprise a plurality of neurostimulation electrodes.

3. The system of claim 1 wherein the first and second lumens comprise different size diameters.

4. The system of claim 1 wherein the IPG is adapted to use at least one defibrillation electrode as an anode for neurostimulation pulses applied using one or more neurostimulation electrodes.

5. The system of claim 1 wherein the neurostimulation electrodes of the first and second flat surfaces possess respective lengths between 1 mm to 6 mm.

6. The system of claim 1 wherein the defibrillation electrodes of the first and second flat surfaces possess respective lengths between 15 mm to 50 mm.

7. The system of claim 1 wherein each of the first and second flat surfaces are connected to a respective opposing surface with a rounded shape.

* * * * *